US012146872B2

(12) United States Patent  
Maiorano et al.

(10) Patent No.: US 12,146,872 B2  
(45) Date of Patent: Nov. 19, 2024

(54) METHOD AND SYSTEM FOR MONITORING AND IDENTIFYING THE WELD QUALITY ON METALLIC COMPONENTS

(71) Applicant: HITACHI RAIL S.P.A., Naples (IT)

(72) Inventors: Francesco Maiorano, Naples (IT); Alessandro Di Mari, Naples (IT); Gualtiero Gailli, Naples (IT)

(73) Assignee: HITACHI RAIL S.P.A., Naples (IT)

( * ) Notice: Subject to any disclaimer, the term of this patent is extended or adjusted under 35 U.S.C. 154(b) by 777 days.

(21) Appl. No.: 17/215,532

(22) Filed: Mar. 29, 2021

(65) Prior Publication Data

US 2021/0341451 A1 Nov. 4, 2021

(30) Foreign Application Priority Data

Mar. 30, 2020 (IT) .................. 102020000006643

(51) Int. Cl.
*G01N 33/207* (2019.01)
*B23K 31/12* (2006.01)
(Continued)

(52) U.S. Cl.
CPC ............. *G01N 33/207* (2019.01); *G06N 5/01* (2023.01); *G06N 5/04* (2013.01); *G06N 20/20* (2019.01)

(58) Field of Classification Search
CPC .... B23K 31/02; B23K 31/125; G01N 33/207; G06N 20/20; G06N 5/01; G06N 5/04
See application file for complete search history.

(56) References Cited

U.S. PATENT DOCUMENTS

| 3,271,558 A * | 9/1966 | Davis ..................... B23K 9/095 |
| | | 219/130.21 |
| 2011/0192825 A1 | 8/2011 | Calefati |

(Continued)

FOREIGN PATENT DOCUMENTS

| CA | 2594819 A1 * | 1/2008 | ........... B23B 49/001 |
| CN | 102049613 A  * | 5/2011 | |

(Continued)

OTHER PUBLICATIONS

Zhang et al., Robust pattern recognition for measurement of three dimensional weld pool surface in GTAW, 2013, Springer, J Intell Manuf (2015) 26:659-676, DOI 10.1007/s10845-013-0825-z (Year: 2013).*

(Continued)

*Primary Examiner* — Mi'schita' Henson  
(74) *Attorney, Agent, or Firm* — Leason Ellis LLP

(57) ABSTRACT

A method and system for monitoring and identifying the quality of a welding performed by a welding machinery on a metallic component, which includes establishing a plurality of classes that describe possible weld defects on the metallic component; identifying a plurality of features that are relative to the functioning of the welding machinery; acquiring the values assumed by the plurality of features during the execution of a current welding on a metallic component; and processing the values assumed by the plurality of features during the execution of the current welding to establish the probabilities of the future outcome of the welding of belonging to each of the classes of the plurality of classes.

13 Claims, 5 Drawing Sheets

(51) Int. Cl.
   *G06N 5/01*        (2023.01)
   *G06N 5/04*        (2023.01)
   *G06N 20/20*       (2019.01)

(56) References Cited

U.S. PATENT DOCUMENTS

| | | | | |
|---|---|---|---|---|
| 2013/0248505 | A1* | 9/2013 | Anayama | B23K 11/115 |
| | | | | 219/130.01 |
| 2014/0332514 | A1 | 11/2014 | Holverson et al. | |
| 2015/0056585 | A1* | 2/2015 | Boulware | B23K 31/125 |
| | | | | 434/234 |
| 2017/0151634 | A1* | 6/2017 | Witney | G01N 29/04 |
| 2018/0250763 | A1 | 9/2018 | Kita et al. | |

FOREIGN PATENT DOCUMENTS

| | | | | |
|---|---|---|---|---|
| EP | 1083018 | A2 * | 3/2001 | B23K 11/061 |
| EP | 2628561 | A1 * | 8/2013 | B23K 11/115 |
| WO | WO-2016153562 | A1 * | 9/2016 | B23K 37/0276 |
| WO | WO 2020/038389 | | 2/2020 | |

OTHER PUBLICATIONS

"Cross-Validation" Refaeilzadeh P. et al. (Jan. 2009, DOI: 10.1007/978-0-387-39940-9_565, https://link.springer.com/referenceworkentry/10.1007%2F978-1-4899-7993-3_565-2).

"Robust impurity measures in decision trees" Aluja-Banet et al. (1998; DOI: 10.1007/978-4-431-65950-1_2, https://link.springer.com/chapter/10.1007/978-4-431-65950-1_21).

A. Sumesh et al: Use of Machine Learning algorithms for Weld Quality Monitoring using Acoustic Signature, Dec. 2015, XP002801523, Retrieved from the Internet: URL:I0.1016/j.procs.2015.04.042, https://core.ac.uk/download/pdf/82463752.pdf, * the whole document *.

Leo Breiman, "Random Forests", Machine Learning, 45, 5-32, Oct. 2001.

Bergstra et al., "Random Search for Hyper-Parameter Optimization", Journal of Machine Learning Research 13 (Feb. 2012) 281-305.

* cited by examiner

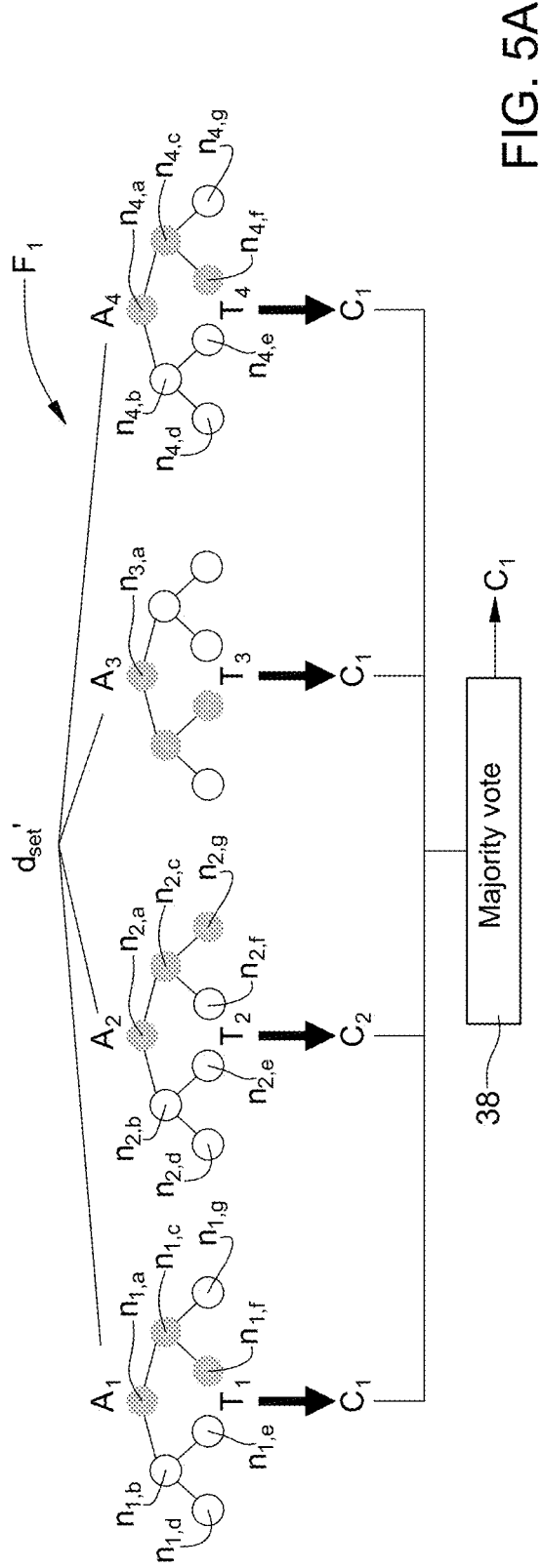
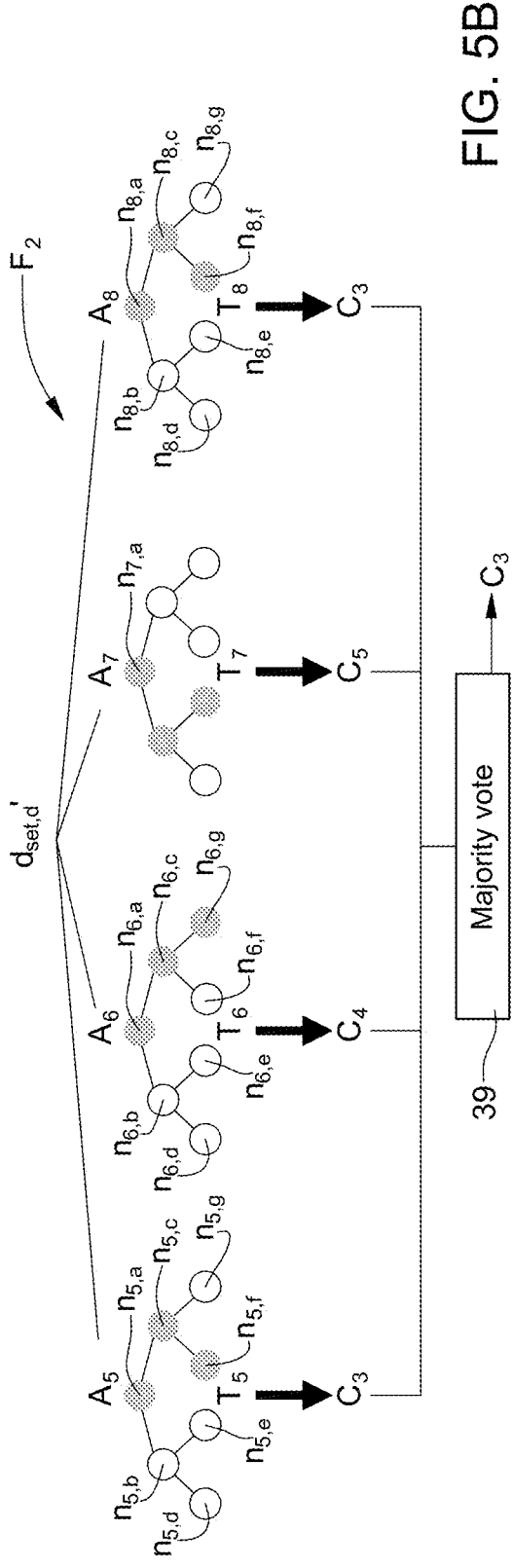
FIG. 5A
FIG. 5B

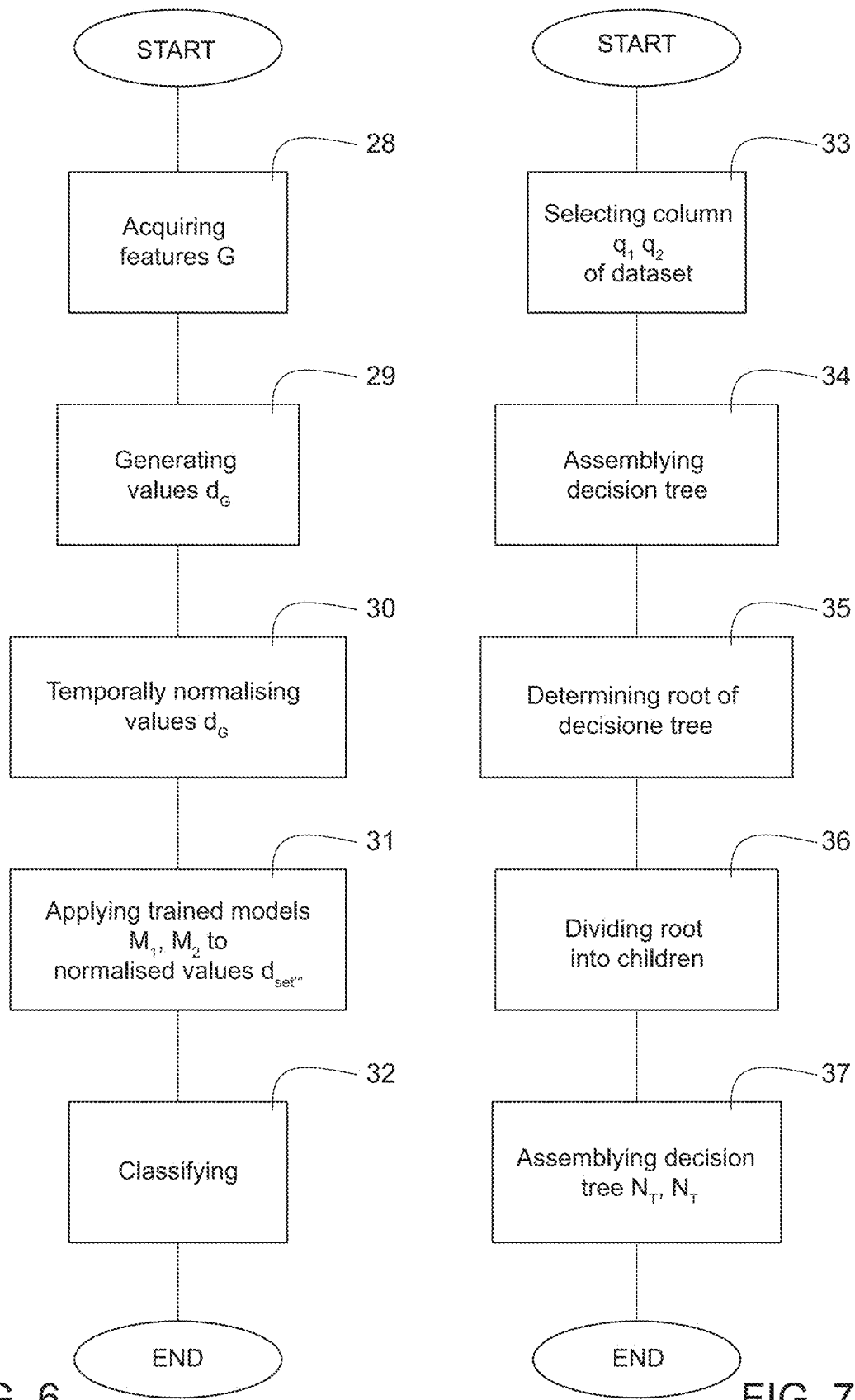

METHOD AND SYSTEM FOR MONITORING AND IDENTIFYING THE WELD QUALITY ON METALLIC COMPONENTS

CROSS-REFERENCE TO RELATED APPLICATIONS

This patent application claims priority from Italian Patent Application No. 102020000006643 filed on Mar. 30, 2020, the entire disclosure of which is incorporated herein by reference.

TECHNICAL FIELD

The present invention relates to a method and to a system for monitoring and identifying the weld quality on metallic components. In particular and without any loss of generality, hereinafter reference is made to metallic components such as, for example, mechanical components (such as, for example, longeron) used in applications such as railway, for example for manufacturing frames for bogies.

PRIOR ART

Welding machines are known, for example dedicated industrial robots, adapted to perform welds on metallic components; specifically, such metallic components are, for example, mechanical components, for example carbon steel longerons and are used in applications such as railway applications (for example, for manufacturing frames for bogies).

Typically, robotised welding machines are configured to perform a plurality of welding operations, which are coded in an algorithm loaded on a computer support (such as, for example, a dedicated processor); in particular, the computer support is connected to the robotised welding machinery and configured to control it by means of the aforementioned algorithm so as to make welds on the aforementioned metallic components.

However, during the welding process of one or more metallic components, the robotised welding machinery can produce weld defects on the final metallic components due to the discordance between the nominal conditions and the real conditions that actually occur during the aforementioned welding process. In particular, there are different types of weld defects, such as, for example, stuck welds, points where the fusion of the material for the weld did not take place (hereinafter referred in short to as lack of fusion) and inclusions of oxide in the weld point (hereinafter referred in short to as inclusions).

Typically, the aforementioned defects are detectable only downstream of the welding process by means of non-destructive controls (for example, detection methods based on ultrasounds), since it is complex to identify such defects with the naked eye during the welding process. Based on the results of the aforementioned controls, a qualified expert of a quality control body thus determines if a defect is or is not present on different areas of the final metallic component and, in the presence of a weld defect on one or more metallic components, said expert classifies said defect by type.

Known solutions provide methods for monitoring and predicting a weld quality based on monitoring and prediction algorithms, loaded for example on the computer support connected to the robotised welding machinery; in particular, such algorithms are adapted to evaluate a dataset relative to the metallic components and, based thereon, identify and classify the weld defects, if the latter are present.

An example of one of the aforementioned algorithms is described in the article "Use of Machine Learning Algorithms for Weld Quality Monitoring using Acoustic Signature" by Sumesh A. et al. (2015, DOI: 10.1016/j.procs.2015.04.042, https://core.ac.uk/download/pdf/82463752.pdf), in which a plurality of time series deriving from different features monitored during the welding operations are classified based on three classes, in particular based on the type of weld defect (specifically, the absence of defect, the lack of fusion and burn through). In particular, the algorithm receives at the input a sound signal recorded by means of an external microphone, arranged in proximity of the welding machinery, and converts it into magnitude; in detail, such sound signal is indicative of the noise emitted by the welding machinery during one or more welding operations of the welding process. Furthermore, the aforementioned algorithm is configured to receive at the input, besides the sound signal from the external microphone, a voltage, a wire speed and a measurement of the applied thermal flow, which are relative to the functioning modes of the welding machinery during the welding operations and are detected by corresponding sensors mounted on the welding machinery. It should be noted that the aforementioned sound signal is acquired in a protected environment, i.e. in an environment without significant external noises which can disturb the sound signal acquired for the execution of the algorithm. Therefore, such algorithm, based on the aforementioned input data, works so as to generate a prediction, i.e. a classification of the aforementioned features (relative to the considered metallic components) and provide the result of the aforementioned prediction/classification as output data to the user.

In light of the aforementioned considerations, the aforementioned known algorithm is not suitable for the industrial use, since the welding machinery is arranged in a non-protected environment; therefore, the acquired sound signal can be disturbed by undesired noises, thus making it not much representative of the noise made by the welding machinery during the welding operations. Consequently, a prediction based on the aforementioned disturbed sound signal will be disturbed as well and, thus, misleading for the purpose of monitoring the welding operations of the aforementioned metallic components.

Furthermore, such known algorithm does not allow detecting volumetric weld defects since it is trained only on visual defects, i.e. on defects of surface nature.

In addition, the welding process is complex per se: in particular, it depends, for example, on a high number of features, on the variability of the work programme, on the preparation of the metallic component before the welding and on further factors not listed herein. Therefore, also the classification suffers from a certain level of uncertainty due to the randomness that characterises the welding process.

DESCRIPTION OF THE INVENTION

The object of the present invention is to provide a method and a system for monitoring and predicting that overcome the drawbacks of the prior art.

According to the present invention, a method and a system for monitoring and predicting the weld quality on metallic components are provided, as claimed in the appended claims.

The claims describe embodiments of the present invention forming integral part of the present description.

BRIEF DESCRIPTION OF THE DRAWINGS

To better understand the present invention, a preferred embodiment thereof is now described, by way of mere non-limiting example, with reference to the accompanying drawings, wherein:

FIGS. 5A and 5B schematically show respective random forests and classification modalities relative to the classification step of FIG. 4;

FIG. 6 shows a flow chart of a second step of the present method, subsequent to the first step of FIG. 2; and FIG. 7 shows a flow chart of a building of a random forest of a step of the method of FIG. 4.

PREFERRED EMBODIMENTS OF THE INVENTION

Figure 1:
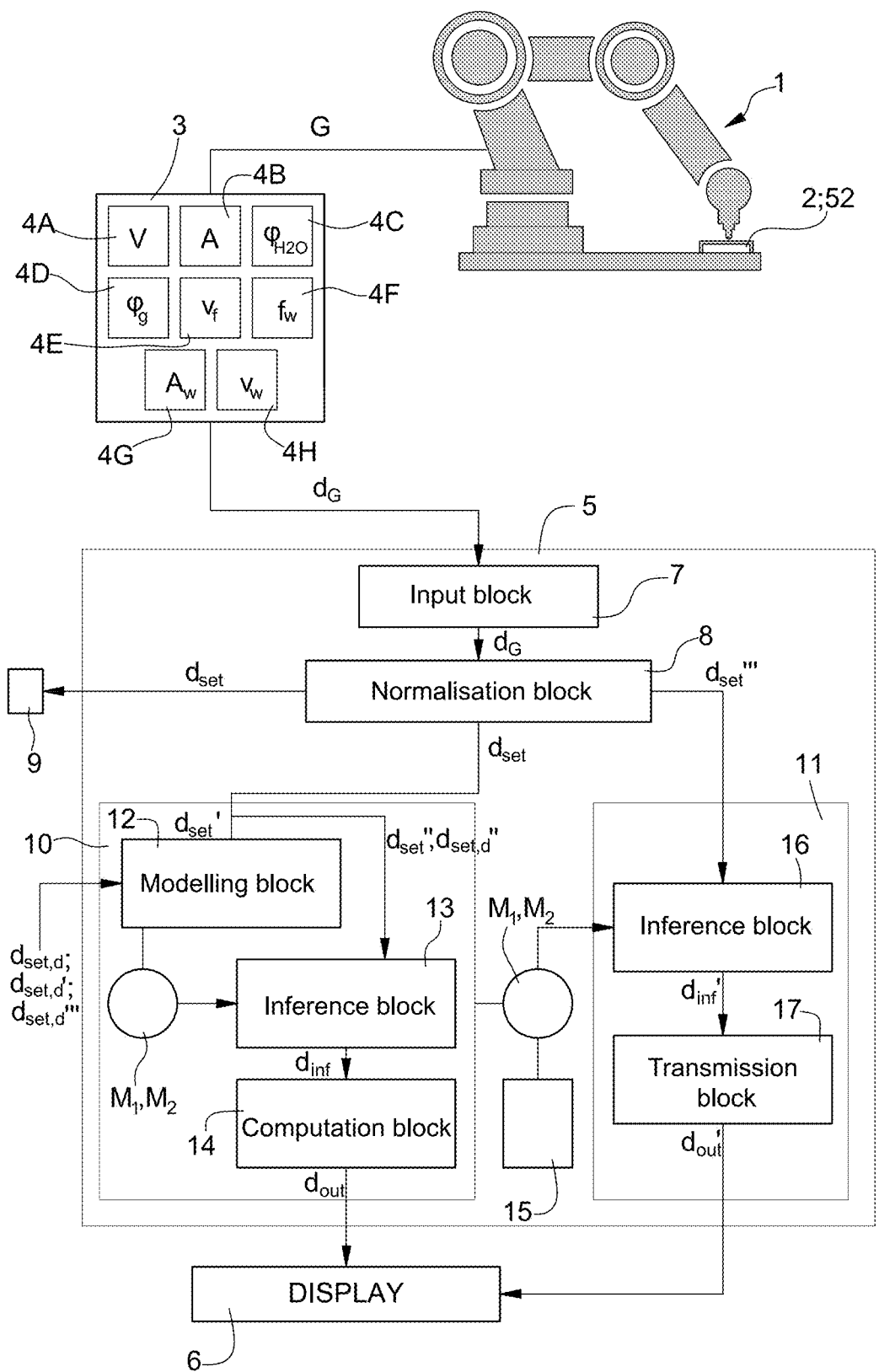
FIG. 1 schematically shows the present system for monitoring and predicting coupled to a welding machinery for the welding of metallic components.

FIG. 1 shows a welding machinery 1, in particular an industrial welding robot, configured to perform welding operations on metallic components, in particular mechanical components, for example, of carbon steel, for applications such as railway applications.

In particular, as better described in the following, it is assumed that, in a first operating step, described in further detail in the following with reference to FIG. 2, the welding machinery 1 operates on first metallic components 2 (one schematically shown in FIG. 1), which are, at the end of the welding process, inspected by means of known techniques (for example, by means of detection methods based on ultrasounds) and labelled by specialised experts with labels relative, for example, to the presence/absence of a defect and, in the case of presence, to the type of defect detected. In other words, the first metallic components 2 represent a set of sample metallic components pre-classified according to a plurality of classes C, which are relative both to the presence/absence of weld defects (classification based on two classes, indicated as $C_1$ and $C_2$ and representing the presence and, respectively, the absence of weld defects) and, for the sample metallic components having defects, to the type of weld defect identified (classification based on a plurality of classes, herein on three classes, indicated as $C_3$-$C_5$ and representing inclusions, lack of fusion and stuck welds); furthermore, the aforementioned metallic components 2 pre-classified in such manner are used for determining trained models $M_1$, $M_2$, respectively relative to the aforementioned classifications based on two and on three classes and which are obtained according to the modalities more specifically described in the following with reference to FIGS. 4, 5A-5B and 7.

It is further assumed that, in a second operating step, subsequent to the aforementioned first operating step, described more specifically in the following with reference to FIG. 6, the welding machinery 1 operates on second metallic components 52 (one schematically shown in FIG. 1), which represent a set of unknown metallic components, i.e. metallic components whose labelling is not known a priori and is determined by means of the trained models $M_1$, $M_2$ obtained in the first operating step.

With reference to FIG. 1, the welding machinery 1 comprises sensor elements 3, which are mounted on the welding machinery 1 and each of which is adapted to detect a respective feature G and to generate respective values $d_G$, each of which represents a value assumed by the corresponding features G when detected by the respective sensor elements 3; in particular, the features G are indicative of respective physical quantities that temporally describe each welding operation on the metallic components 2, 52. In the embodiment of FIG. 1, the sensor elements 3 are eight, are indicated with the reference numerals 4A-4H and are configured to detect, as features G, the sampled values of: a voltage V at the ends of the welding arc, a welding current A, a flow of cooling water ($H_2O$) $\varphi_{H2O}$, a shielding gas flow $\varphi_g$ for the weld pool, a feeding speed $v_f$ of the filler wire, a frequency $f_w$ of the kinematic oscillation of a welding torch, the amplitude $A_w$ of the oscillation itself and, a feeding speed $v_w$ of the torch.

It should be noted that, depending on the values assumed by the features G, determined by the welding machinery 1 (in particular, by the sensor elements 3) in the time instants $t_k$ and depending on the type of preparation process of the metallic components 2, 52 (for example, by means of preparation processes carried out by hand and comprising a brushing step and/or the application of preliminary welding spots, the latter used for keeping adjacent metallic components 2, 52 close during the welding process), the welding process of the metallic components 2, 52 varies, thus determining different results in terms of weld defects on the aforementioned metallic components 2, 52; in other words, different combinations of the values of the aforementioned features G, in association with different combinations of preparation processes of the metallic components 2, 52 to be welded, determine a good or bad weld and have a non-negligible influence on the quality of the final weld of the aforementioned metallic components 2, 52.

The welding machinery 1, in particular by means of the sensor elements 3, is operatively coupled to a system for monitoring and classifying (in the following indicated as system) 5, which is configured to receive the values $d_G$ determined by the sensor elements 3 and perform the aforementioned method for monitoring and predicting, the latter described more specifically in the following. In particular, the system 5 is a classifier system, i.e. a computer support, for example a processor, connected to the welding machinery 1. The system 5 is configured to execute an algorithm that implements the aforementioned method for monitoring and predicting which allows classifying according to a classification based on two and, subsequently, on three classes (i.e. by means of the trained models $M_1$, $M_2$) the values $d_G$ relative to the metallic components 2, 52.

In further detail, the system 5 comprises: an input block 7, coupled to the welding machinery 1 (in particular, to the sensor elements 3) and configured to receive the values $d_G$ relative to the features G associated with the metallic components 2, 52; a normalisation block 8, coupled to the input block 7 and configured to execute a pre-processing and standardising step adapted to temporally normalise the values $d_G$ according to the modes described more specifically in the following, so as to generate normalised values $d_{set}$ and $d_{set}'''$ relative to the metallic components 2 and, respectively, 52; a training block 10, coupled to the normalisation block 8 and configured to receive the normalised values $d_{set}$ relative to the metallic components 2, which are used for the determination of the trained models $M_1$, $M_2$; and a classification block 11, coupled to the normalisation block 8 and configured to receive the normalised values $d_{set}'''$ relative to the metallic components 52, as well as the trained models $M_1$, $M_2$ so as to obtain the classifications based on two and on three classes of the aforementioned metallic components 52.

Specifically, the training block 10 is active in the first operating step and the classification block 11 is active in the second operating step. In other words, the training block 10 is active when the system 5 operates for determining the trained models $M_1$, $M_2$ (i.e. when the values $d_G$ are relative to the metallic components 2) and verifying the classification quality thereof; otherwise, the classification block 11 is active when the welding machinery 1 operates on the values $d_G$ relative to the metallic components 52.

The training block 10 comprises: a modelling block 12, coupled to the normalisation block 8 and configured to receive a first group of normalised values $d_{set}'$, the latter belonging to the normalised values $d_{set}$ and being relative to a group of metallic components 2 (indicated in the following as first group of metallic components 2), and the plurality of classes C and to determine the trained models $M_1$, $M_2$ based on the aforementioned first group of normalised values $d_{set}'$ and on the aforementioned plurality of classes C; an inference block 13, coupled to the modelling block 12 and to the normalisation block 8 and configured to receive a second group of normalised values $d_{set}''$, independent of the first group of normalised values $d_{set}'$ and also belonging to the normalised values $d_{set}$, relative to a group of metallic components 2 (indicated in the following as second group of metallic components 2) whose labelling is known a priori but is not provided to the inference block 13, and to generate inference data $d_{inf}$, indicative of the classifications made by the trained models $M_1$, $M_2$ when applied to the second group of normalised values $d_{set}''$; and a computation block 14, coupled to the inference block 13 and configured to receive the inference data $d_{inf}$ and generate corresponding output data $d_{out}$ indicative of the quality of the classification made by the trained models $M_1$, $M_2$ when applied to the second group of normalised values $d_{set}''$, based on the labelling known a priori.

In addition, the training block 10 is coupled to a memory 15, which is configured to store the trained models $M_1$, $M_2$ determined in the first operating step; in an embodiment, not shown herein, the memory 15 can be implemented on a physical support defined by the hardware support 9 described in the following.

In addition, the normalisation block 8 is configured to transmit the normalised values $d_{set}$ to a dedicated hardware support 9 for the storage, connected to the aforementioned normalisation block 8 by means of a real-time connection, for example by means of communication protocol OPC-UA (OPC Unified Architecture). In further embodiments not shown, the connection between the hardware support 9 and the normalisation block 8 can also be deferred, i.e. the normalised values $d_{set}$ are stored only at the end of one or more welding operations performed by the welding machinery 1.

The classification block 11 comprises: an inference block 16, coupled to the normalisation block 8 and configured to receive, when used in the second operating step, the normalised values $d_{set}'''$ relative to the metallic components 52 from the normalisation block 8 and the trained models $M_1$, $M_2$ from the memory 15 and to apply the latter to the normalised values $d_{set}'''$ relative to the metallic components 52 so as to generate corresponding inference data $d_{inf}'$; and a transmission block 17, coupled to the inference block 16 and configured to receive the inference data $d_{inf}'$ and determine corresponding output data $d_{out}'$. In particular, the inference data $d_{inf}'$ are indicative of a vote percentage for each class of the plurality of classes C associated with each metallic component 52. Starting from the vote percentages for each class belonging to the plurality of classes C, the class of the plurality of classes C determined by each trained model of the trained models $M_1$, $M_2$ with the higher percentage is selected as classification output datum $d_{out}'$.

Furthermore, the system 5 is coupled to a display 6, configured to show, in the first operating step, the output data $d_{out}$ relative to the second group of metallic components 2 and, in the second operating step, the second output data $d_{out}'$ relative to the metallic components 52; in particular, the display 6 allows making displayable the aforementioned output data $d_{out}$ and $d_{out}'$ of the metallic components 2, 52 to a user (for example, a specialised operator) so as to inform said user of the classification capability of the trained models $M_1$, $M_2$ in the first and in the second operating steps.

The first step of the aforementioned method for monitoring and predicting is now described with reference to FIG. 2; in particular, the first step of the aforementioned method for monitoring and predicting comprises a training step and an inference step, subsequent to each other and described with reference to the modelling blocks 12 and, respectively, to the inference 13 and computation 14 blocks.

Initially, step 18, the sensor elements 3 detect the values of the features G associated with the metallic components 2 in a corresponding time interval $\Delta t$ and with respective sampling steps $p_s$. In particular, with reference to the embodiment of FIG. 1, the features G comprise a respective voltage V at the ends of the welding arc, a respective welding current A, a respective flow of cooling water ($H_2O$) $\varphi_{H2O}$, a respective shielding gas flow $\varphi_g$ for the weld pool, a respective feeding speed $v_f$ of the filler wire, a respective frequency $f_w$ of the kinematic oscillation of the torch, the respective amplitude $A_w$ of the oscillation itself and, a respective feeding speed $v_w$ of the torch relative to the welding machinery 1 when it operates on the metallic components 2. Furthermore, the time interval $\Delta t$ represents the time used by the welding machinery 1 for performing the welding operations on each metallic component 2; specifically, each time instant $t_k$ (k being a natural index) represents a time instant within the welding interval $\Delta t$ of the metallic component 2 analysed. Therefore, the values $d_G$ and the time instants $t_k$ are correlated with each other and are representative of respective metallic components 2.

Subsequently, the sensor elements 3 generate the values $d_G$ relative to the aforementioned features G and to each metallic component 2 at the time instant $t_k$, and transmit them together with the corresponding values of time instants $t_k$ to the system 5, which receives them at the input block 7 (step 19).

Then, step 20, the input block 7 transmits the values $d_G$ received to the normalisation block 8, which temporally normalises by means of the application of an interpolation algorithm of the time instants $t_k$ so as to smooth the sampling steps $p_s$ associated with the features G; for example, the normalisation block 8 executes a linear or polynomial interpolation algorithm for executing the aforementioned temporal normalisation. More specifically, the normalisation allows uniforming the interval of values that the aforementioned features G relative to the aforementioned metallic components 2 can assume.

In some embodiments, not shown herein, the system 1 is devoid of the normalisation block 8.

The normalisation step carried out by the normalisation block 8 consequently generates the normalised values $d_{set}$, which represent as well the features G associated with the metallic components 2; more specifically, the normalised values $d_{set}$ are generated in order to allow a better execution of the training and inference steps by the modelling block 12 and, respectively, the inference block 13.

The aforementioned operations, described with reference to the steps 18-20, are repeated up to the end of the welding operations of the metallic components 2. The latter are then inspected with known techniques (for example, inspection through ultrasounds) and classified according to the plurality of classes C by a specialised expert based on the results obtained by the inspection; in particular, the classification is based on two (presence/absence, i.e. the classes $C_1$ and $C_2$) and, in the case of presence of the defect (label "presence", for example associated with the class $C_1$), on three classes (type of defect, i.e. the classes $C_3$, $C_4$ and $C_5$). In other words, the labels, relative to the classification modality of the weld defects on each metallic component 2 are known a priori, are associated with a corresponding time instant $t_k$ and are provided to the modelling block 12 of the training block 10 for the determination of the trained models $M_1$, $M_2$.

To summarise, the normalised values $d_{set}$ are representative of record temporal series. Each record is composed of the time instant $t_k$, belonging to the time interval $\Delta t$, of the set of the corresponding values of the features G at the same time instant $t_k$ and of the corresponding labels.

Figures 3, 4:
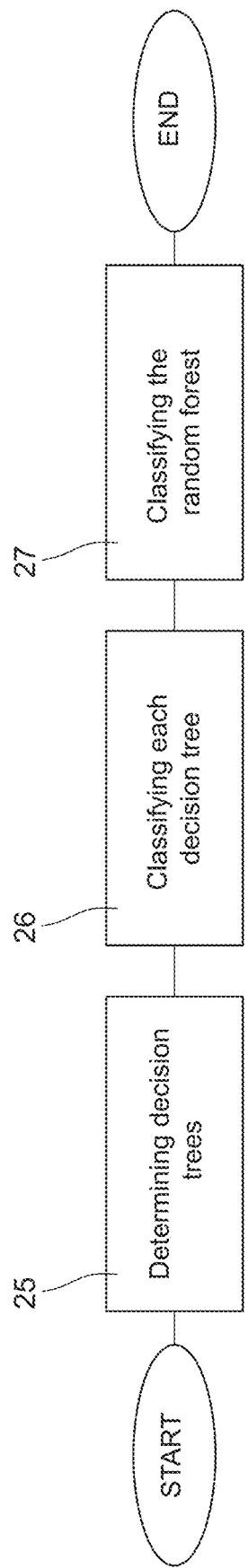
FIG. 3 schematically shows a representation of normalised data obtained in one of the steps of the first step of the method for monitoring and predicting.
FIG. 4 shows a flow chart of a classification step of the first step of the method of FIG. 2.

FIG. 3 schematically shows an example of representation of the aforementioned normalised values $d_{set}$, in particular tabular, as stored in the aforementioned hardware support 9, wherein they are stored subsequent to the aforementioned pre-processing and normalisation step. In particular, according to the embodiment shown in FIG. 3, the welding process of each metallic component 2 consists of a number N' of rows relative to the time instants $t_k$ and of a number M' of columns, relative to the values $d_G$ associated with the metallic components 2 and with the relative labels associated by the expert. Therefore, as apparent by what shown in FIG. 3, to each time instant $t_k$, respective values $d_G$ correspond, i.e. each time instant $t_k$ of the welding process of a metallic component 2 is represented as a vector in a multidimensional space, herein eight-dimensional, of values $d_G$ relative to corresponding features G and to which labels (i.e. one or more classes of the plurality of classes C) are associated. In other words, the normalised values $d_{set}$ represent a dataset which is used by the training block 10 for the determination and the evaluation of the trained models $M_1$, $M_2$.

The training and inference steps of the present method for monitoring and predicting of the first operating step are now described, respectively executed by the modelling block 12 and by the inference and computation blocks 13 and 14 of the training block 10 with reference to FIGS. 2, 4, 5A-5B and 7.

Figure 2:
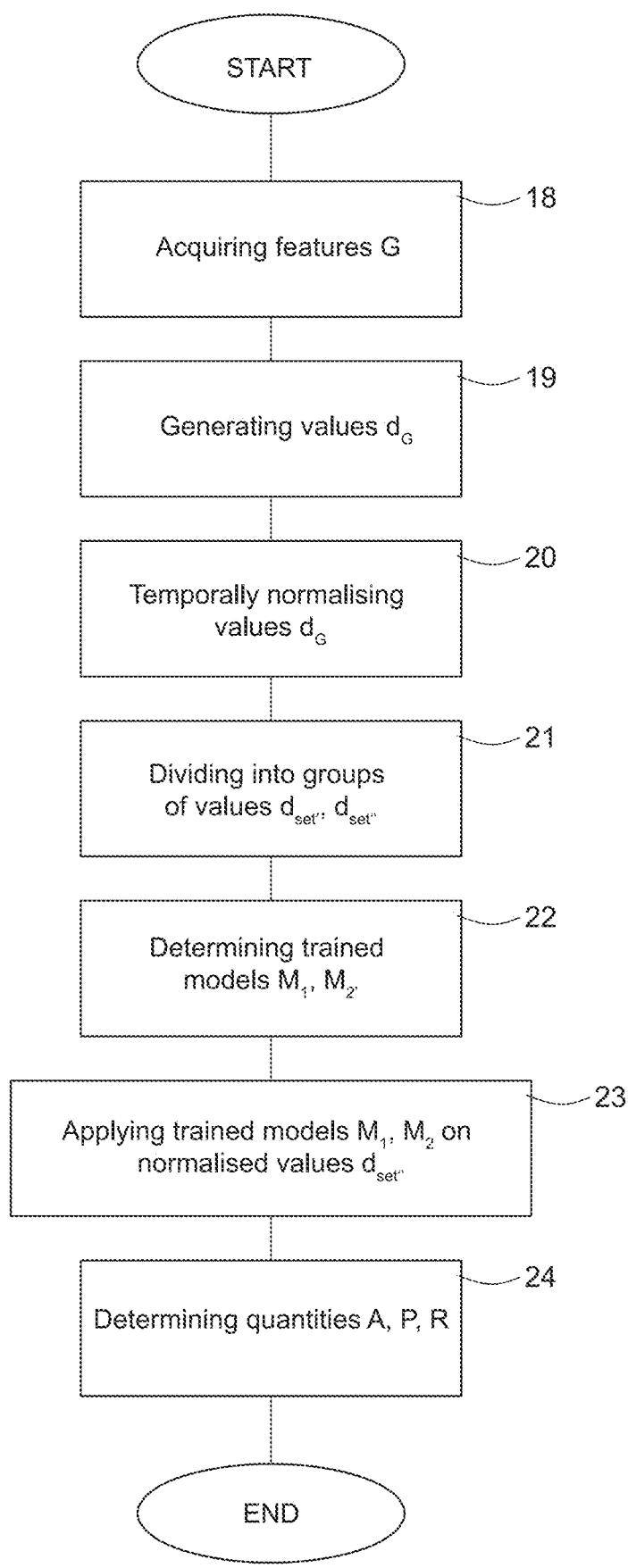
FIG. 2 shows a flow chart of a first step of the present method for monitoring and predicting.

In particular, with reference to FIG. 2, step 21, the training block 10 divides the normalised values $d_{set}$ relative to the metallic components 2 into the first and second groups of normalised values $d_{set}'$, $d_{set}''$, which are respectively used by the modelling block 12 and by the inference block 13; in particular, the first and second groups of normalised values $d_{set}'$, $d_{set}''$ are representable as well in tabular form as described previously with reference to FIG. 3 and relatively to the normalised values $d_{set}$. More specifically, in the case of classification based on two classes, the division of the aforementioned normalised values $d_{set}$ is such that the first group of normalised values $d_{set}'$ represents 80% of the normalised values $d_{set}$ and the second group of the normalised values $d_{set}''$ represents the remaining 20% of the normalised values $d_{set}$.

Subsequently, step 22, the first group of normalised values $d_{set}'$ is used as dataset for the determination of the trained model $M_1$, i.e. for the determination of the decision rules or, alternatively, of the decision regions in a vector space (i.e., the vector space defined by the aforementioned multidimensional vectors, herein eight-dimensional) that adjust the relation between the metallic components 2 (which, as previously anticipated, are represented by the time intervals $\Delta t$) and the labels associated thereto. The determination modes of the trained model $M_1$ are described more specifically in the following with reference to FIGS. 4, 5A and 7.

The classification based on two classes made by the aforementioned trained model $M_1$ thus determines a division of the first group of normalised values $d_{set}'$ into values with label indicative of the presence of a weld defect (in the following, indicated as defect values $d_{set,d}$), identified with the class $C_1$, and values with label indicative of the absence of a weld defect, identified with the class $C_2$.

In addition, as better described in the following, the first group of normalised values $d_{set}'$ is further used for validating the trained model $M_1$; for example, the validation is executed by means of the K-fold cross-validation method.

Subsequently, the defect values $d_{set,d}$ are thus used for the determination of the trained model $M_2$; therefore, analogously to the normalised values $d_{set}$ (steps 21 and 22 of FIG. 2), the defect values $d_{set,d}$ are divided into a first and a second group of defect values $d_{set,d}'$, $d_{set,d}'''$. More specifically, in the case of classification based on two classes, the division of the aforementioned values $d_{set,d}$ is such that the first group of normalised values $d_{set,d}'$ represents 70% of the defect values $d_{set,d}$ and the second group of defect values $d_{set,d}'''$ represents the remaining 30% of the defect values $d_{set,d}$. It should be noted that the defect values $d_{set,d}$ (i.e. the first and the second groups of defect values $d_{set,d}'$, $d_{set,d}'''$) are representable analogously to the normalised values $d_{set}$, i.e. in tabular manner (as shown in FIG. 3 for the normalised values $d_{set}$); in such case, the number of rows of the table will be equal to N' and will be below the number N' relative to the normalised values $d_{set}$, since not all the normalised values $d_{set}$ belong to the first group of normalised values $d_{set}'$ and not all are classified as having defects, while the number of columns M' remains the same.

Furthermore, with reference to the step 22, the first group of defect values $d_{set,d}'$ is used as dataset for the determination of the trained model $M_2$, i.e. for the determination of the decision rules or, alternatively, of the decision regions in a vector space (i.e. the vector space defined by the aforementioned multidimensional vectors, herein eight-dimensional) that adjust the relation between the metallic components 2 (which, as previously anticipated, are represented by the time intervals $\Delta t$) and the labels associated thereto. The determination modes of the trained model $M_2$ are described more specifically in the following with reference to FIGS. 4, 5B and 7. On the other hand, the second group of defect values $d_{set,d}'''$ is used for a validation step of the trained model $M_2$, for example by means of the K-fold cross-validation method, as better described in the following.

In other words, the trained models $M_1$, $M_2$ represent mathematical models that adjust the relation between the time instants $t_k$ and the values $d_G$ of the features G associated with the sample metallic components 2.

In particular, in the present embodiment of the aforementioned method, the system 5 determines in subsequent steps the aforementioned trained models $M_1$, $M_2$ by means of a supervised machine learning algorithm based on the random forest RF method, which is described in the following with reference to FIGS. 4 and 7. In particular, such algorithm is of ensemble type and is based on a methodology described, for example, in the article "Random forests" by Breiman L. (2009, DOI: 10.1023/A:1010933404324, https://link.springer.com/article/10.1023/A:1010933404324), which is based on the building of random forests of decision trees, not correlated to each other and adapted to produce respective classifications; furthermore, the classification of the random forest is determined in a vote policy according to the classifications made by the single decision trees.

In particular and with reference to FIG. 4, the steps 25-27 are initially carried out to obtain the trained model $M_1$ and, subsequently, for the determination of the trained model $M_2$, whose determination depends on the result of the classification obtained by the trained model $M_1$. Therefore, in the following a first modelling step, wherein the modelling block 12 determines the trained model $M_1$ according to the modes described with reference to FIGS. 4 and 7; and a second modelling step, subsequent to the first modelling step and wherein the modelling block 12 determines the trained model $M_2$ according to the modes described with reference to FIGS. 4 and 7, in particular according to the results obtained in the first modelling step, are described.

More specifically, the modelling block 12 is configured to generate optimised trained models $M_1$, $M_2$; in particular, such optimisation is carried out herein by means of a hyper-parameter tuning, which is executed, for example, analogously to what described in the article "Random search for hyper-parameter optimization" by Bergstra J. et al. (Journal of machine learning research 13 Feb. (2012): 281-305, http://www.jmlr.org/papers/v13/bergstra12a.html). In particular, the hyper-parameter tuning allows acting on the latter so as to optimise the effectiveness of the aforementioned machine learning algorithm.

In the present embodiment, the system 10 defines a set of hyper-parameters J, comprising, for example, the number of trees in the random forest (herein, indicated as numbers $N_T$, $N_T'$, equal for example to four and indicated in FIGS. 5A, 5B with references $T_1$-$T_4$ and $T_5$-$T_8$, and relative to respective random forests $F_1$, $F_2$, schematically shown in FIGS. 5A and 5B respectively and relative respectively to the classification based on two classes and to the classification based on three classes, i.e. to the trained models $M_1$ and $M_2$, respectively), a maximum height or depth H of the trees of the random forest (i.e. for example, the trees $T_1$-$T_4$ and $T_5$-$T_8$), the number of metallic components 2 of the set of values considered (i.e. the number of metallic components 2 represented by the first group of normalised values $d_{set}'$ or by the first group of defect values $d_{set,d}'$, which are thus the rows of the respective tables representative of the aforementioned first groups of normalised values $d_{set}'$ and of defect values $d_{set,d}'$ and are indicated also as bootstrap), the number of features G of the set of values used for the building of sets $A_1$-$A_8$ of features G used for the building of the trees $T_1$-$T_4$ and $T_5$-$T_8$ of the respective random forests $F_1$, $F_2$ (i.e. the number of columns of the respective tables representative of the aforementioned first groups of normalised values $d_{set}'$ and of defect values $d_{set,d}'$), the minimum number of features G that must be located in a leaf of each decision tree $T_1$-$T_8$, the minimum number of features G required to split a node into children nodes and a criterion of impurity.

It should be noted that the hyper-parameter tuning is iterative, i.e. the modelling block 12 tests different hyper-parameters, which are defined in a range), and determines the best one (for example calculating a metric, such as accuracy, described more specifically in the following, associated thereto); in the present embodiment, the modelling block 12 determines, as best hyper-parameters, the hyper-parameters J, herein six.

In particular, the aforementioned criterion of impurity is determined by the modelling block 12, in particular structuring the aforementioned machine learning algorithm so as to maximise a measure of purity of nodes in each decision tree $T_1$-$T_8$; specifically, the purity of a node of a decision tree $T_1$-$T_8$ is defined in terms of a measure of homogeneity, the latter detectable during the training step from the modelling block 12. More specifically, the modelling block 12 determines the quality of the classification of the aforementioned machine learning algorithm according to the presence of features G associated with metallic components 2 classified with the same class in the nodes of each decision tree $T_1$-$T_8$. In order to produce the aforementioned measure, the modelling block 12 implements a measure of impurity in the nodes of each decision tree $T_1$-$T_8$; with reference to FIGS. 5A, 5B, the modelling block 12 executes the aforementioned measure of impurity in each node $n_{1-8,a-g}$ (shown in FIGS. 5A and 5B, wherein a-g are natural indexes and relative to the number, herein seven, of nodes per tree $T_1$-$T_8$) of the respective decision trees $T_1$-$T_8$ of the respective random forests $F_1$, $F_2$. For example, the aforementioned measure of impurity is executed by means of a Gini Impurity approach, as discussed for example in the article "Robust impurity measures in decision trees" by Aluja-Banet et al. (DOI: 10.1007/978-4-431-65950-1_2, https://link.springer.com/chapter/10.1007/978-4-431-65950-1_21); in particular, the Gini Impurity approach allows determining the discriminating power of each of the features G associated with the metallic components 2 within the machine learning algorithm, producing a ranking relative to the importance of each feature G in the discrimination of each class $C_1$-$C_5$. The aforementioned evaluation of purity by means of the Gini Impurity approach allows identifying the features G that refine the optimisation of the aforementioned machine learning algorithm. In this manner it is possible to identify the features G associated with the metallic components 2 that result less significant for the classification of the metallic components 2 (and, thus, in the second operating step, of the metallic components 52) on the part of the aforementioned machine learning algorithm. In further embodiments, not shown herein, a measurement of impurity is carried out by means of other approaches, such as, for example, Information Gain or Variance Reduction.

In addition to what described in the previous paragraphs, the modelling block 12 is configured, always in the step of hyper-parameter tuning and of maximisation of the purity of the nodes (and, thus, of the evaluation of the criterion of impurity of the nodes), to determine the classification capabilities of the random forest for each metallic component 2 by means of cross-validation techniques; for example, such evaluation is carried out by means of a K-fold cross-validation method, as described for example in the article "Cross-Validation" by Refaeilzadeh P. et al. (2009, DOI: 10.1007/978-0-387-39940-9_565, https://link.springer.com/referenceworkentry/10.1007%2F978-1-4899-7993-3_565-2). In particular, the validation step, which is executed for both trained models $M_1$, $M_2$, allows calculating a plurality of metrics, for example accuracy A, precision P and recall R according to the equations (1), (2) and, respectively, (3) provided hereafter:

$$A = \frac{tp + tn}{tp + tn + fp + fn} \quad (1)$$

$$P = \frac{tp}{tp + fp} \quad (2)$$

$$R = \frac{tp}{tp + fn} \quad (3)$$

where tp is the number of true positives, tn is the number of true negatives, fp is the number of false positives and fn is the number of false negatives. More specifically, accuracy A represents the capability of each model of the trained models $M_1$, $M_2$ to correctly classify the welding process at the temporal instant $t_k$; precision P represents the capability of each model of the trained models $M_1$, $M_2$ not to produce false positives; and recall R represents the capability of each model of the trained models $M_1$, $M_2$ not to produce false negatives.

The calculation of the aforementioned metrics thus allows determining the quality of the classification; in addition, in the step of hyper-parameter tuning, the modelling block 12 is configured to maximise one of the aforementioned metrics, for example the recall R.

In light of what described above, in the embodiment of FIG. 1, the K-fold cross-validation method is applied both to the first group of normalised values $d_{set}'$ for the validation of the trained model $M_1$ and, respectively, to the second group of values $d_{set,d}'''$ for the validation of the trained model $M_2$ during the operations of determination of the aforementioned trained models $M_1$, $M_2$ at the training block 10; therefore, the aforementioned calculation of accuracy A, of precision P and of recall R allow, always within the optimisation procedure, validating the trained models $M_1$, $M_2$, in particular maximising the recall R of each one.

In light of what described above and with reference to FIGS. 2, 4, 5A, 5B and 7, the steps of building the random forests $F_1$, $F_2$ are now described.

With reference to FIG. 4, initially, step 25, the modelling block 12 receives the first group of normalised values $d_{set}'$ and uses them for determining $N_T$ (wherein $N_T$ is a natural number) decision trees, which are not correlated to each other, each of which is formed starting from a random combination of features G. In particular, the first random forest $F_1$ of FIG. 5A is relative to the first group of normalised values $d_{set}'$ comprises the decision trees $T_1$-$T_4$ (i.e. $N_T$ is equal to four) each of which is built using the respective sets $A_1$-$A_4$ of features G (represented by the first group of normalised values $d_{set}'$) generated randomly and is relative to the classification based on two classes $C_1$, $C_2$.

The embodiment of the aforementioned first random forest $F_1$ is obtained according to the modes described with reference to FIG. 7.

Firstly, block 33, the modelling block 12 selects a number $q_1$ of features G (i.e. of columns M' of the tables representative of the aforementioned first groups of normalised values $d_{set}'$) represented by the first group of normalised values $d_{set}'$. In particular, the number $q_1$ is very much below with respect to the number of columns M' of the features G represented by the respective first groups of normalised values $d_{set}'$; in particular, the number $q_1$ is determined based on the height H of the decision trees of the first random forest $F_1$.

Subsequently, block 34, the system 5 builds a decision tree (for example, one of the trees $T_1$-$T_4$ of the first random forest $F_1$) based on the $q_1$ features G extracted in the previous step. In particular, each of the $q_1$ features represents a corresponding set $A_1$-$A_4$.

Subsequently, block 35, the modelling block 12 determines the root of the decision tree determined in the step at the block 34 by means of the aforementioned measure of impurity. For example, the nodes $n_{1-4, a}$ are root nodes for the respective decision trees $T_1$-$T_4$.

Then, block 36, the modelling block 12 splits the root node identified in the step of the block 35 into children nodes (as shown in FIGS. 5A, 5B), such as, for example, the nodes $n_{1-4,b-g}$. Once executed this operation, the modelling block repeats the steps described with reference to the blocks 33-34 until reaching the maximum height H predefined in the selection step of the hyper-parameters J and relative to each tree $T_1$-$T_4$ of the first random forest $F_1$.

Finally, block 37, the modelling block 12 repeats the steps described with reference to the blocks 33-36 so as to obtain the number $N_T$ of decision trees of the first random forest $F_1$.

Subsequently, block 26, each of the decision trees $N_T$ produces, in a manner known per se, a classification of the features G based on two classes ($C_1$ and $C_2$). As shown in FIG. 5A, each decision tree $T_1$-$T_4$ produces a respective class $C_1$, $C_2$, representing whether a weld defect is present or not.

Then, block 27, in order to obtain the trained model $M_1$, based on the single classifications produced by each of the decision trees $N_T$, the modelling block 12 determines the final classification for the first random forest $F_1$ determining the percentage of vote for each class determined by the decision trees $N_T$. In other words, the class that has the highest number of votes (i.e. is in majority with respect to the other classes determined) is determined as winning and associated with the metallic component 2 under exam (in particular, with the vector associated thereto). With reference to FIG. 5A, step 38, the training step 12 executes the aforementioned voting relatively to the first random forest $F_1$ and determines that the most voted class is the class $C_1$.

Therefore, in the welding instants $t_k$ of a single metallic component 2, the classification based on two classes by means of the first random forest $F_1$ determined that in such instants the values assumed by the features G can lead to weld defects in the metallic component 2 classified according to the class $C_1$.

Such operation is thus executed for all the metallic components 2 which are represented by the first group of normalised values $d_{set}'$, thus obtaining a division between metallic components 2 classified as having weld defects (class $C_1$) and metallic components 2 not having weld defects (class $C_2$). In particular, the portion of values of the first group of normalised values $d_{set}'$ representing the metallic components 2 classified as having weld defects represent the defect values $d_{set,d}$.

In addition, as previously anticipated, the first group of normalised values $d_{set}'$ is used for the validation of the trained model $M_1$ which derives from the previously described classification steps through the first random forest $F_1$. \In other words, at the end of the aforementioned steps 25-27 of FIG. 2 and 33-37 of FIG. 7, the modelling block determines the defect values $d_{set,d}$, which are divided into the first and second groups of defect values $d_{set,d}'$, $d_{set,d}'''$; in particular, the first group of defect values $d_{set,d}'$ are employed for determining the second random forest $F_2$ and the relative classification according to the aforementioned classes $C_3$-$C_5$ analogously to what described with reference to the first group of normalised data $d_{set}'$.

Therefore, the operations described with reference to the steps 25-27 of FIG. 4 and 33-37 of FIG. 7 are repeated also for the first group of defect values $d_{set,d}'$.

In particular, step 25, the modelling block 12 receives the first group of defect values $d_{set,d}'$ and uses them for determining decision trees $N_T'$ (wherein $N_T'$ is a natural number), which are not correlated to each other, each of which is formed starting from a random combination of features G. In particular, the second random forest $F_2$ of FIG. 5B is relative to the first group of values $d_{set,d}'$ comprises the decision trees $T_1$-$T_8$ (i.e. $N_T'$ is equal to four) each of which is built using the respective sets $A_1$-$A_8$ of features G generated randomly and is relative to the classification based on three classes $C_3$-$C_5$.

The embodiment of the aforementioned random forest $F_2$ is embodied according to the modes described with reference to FIG. 7.

Firstly, block 33, the modelling block 12 selects a number $q_2$ of features G (i.e. of columns M'−1, excluded the column relative to the labels, the tables representative of the aforementioned first groups of defect values $d_{set,d}'$) represented by the first group of defect values $d_{set,d}'$. In particular, the number $q_2$ is very much below with respect to the number of columns M' of the features G represented by the respective first group of normalised values $d_{set}'$; in particular, the number $q_2$ is determined according to the height H of the decision trees of the second random forest $F_2$. Subsequently, block 34, the system 5 builds a decision tree (for example, one of the trees $T_5$-$T_8$) based on the $q_2$ features G extracted in the previous step. In particular, each of the $q_2$ features represents a corresponding set $A_5$-$A_8$.

Subsequently, block 35, the modelling block 12 determines the root of the decision tree determined in the step at block 34 by means of the aforementioned measure of impurity. For example, the nodes $n_{5-8, a}$ are root nodes for the respective decision trees $T_5$-$T_8$.

Then, block 36, the modelling block 12 splits the root node identified in the step of block 35 into children nodes (as shown in FIGS. 5A, 5B), such as, for example, the nodes $n_{5-8,b-g}$. Once executed this operation, the modelling block repeats the steps described with reference to the blocks 33-34 until reaching the maximum height H predefined in step of selection of the hyper-parameters J and relative to each tree $T_5$-$T_8$ of the second random forest $F_2$.

Lastly, block 37, the modelling block 12 repeats the steps described with reference to the blocks 33-36 so as to obtain the number $N_T'$ of decision trees of the second random forest $F_2$.

Subsequently, block 26, each of the $N_T'$ decision trees produces, in a manner known per se, a classification of the features G based on three classes ($C_3$-$C_5$). As shown in FIG. 5B, each decision tree $T_5$-$T_8$ produces a respective class $C_3$-$C_5$, representing the type of weld defect.

Then, block 27, in order to obtain the trained model $M_2$, based on the single classifications produced by each of the $N_T'$ decision trees, the modelling block 12 determines the final classification for the second random forest $F_2$ determining the percentage of vote for each class determined by the $N_T'$ decision trees. In other words, the class that has the highest number of votes (i.e., is in majority with respect to the other classes determined) is determined as winning and associated with the metallic component 2 under exam (in particular, with the vector associated therewith). With reference to FIG. 5B, step 39, the training block 12 executes the aforementioned voting relatively to the second random forest $F_2$ and determines that the most voted class is the class $C_3$.

Therefore, in the welding instants $t_k$ of a single metallic component 2, the classification based on three classes by means of the second random forest $F_2$ determined that in such instants the values assumed by the features G can lead to weld defects in the metallic component 2 classified according to the class $C_3$.

In addition, as previously anticipated, the second group of defect values $d_{set,d}'''$ is used for the validation of the trained model $M_2$ that derives from the classification steps through the second random forest $F_2$ described previously; in particular, such validation is executed by means of K-fold cross-validation methods, through which accuracy A, precision P and recall R are determined for the aforementioned second group of defect values $d_{set,d}'''$.

Such operation is thus executed for all the metallic components 2 that are represented by the first group of normalised values $d_{set}'$, thus obtaining a division between metallic components 2 based on the type of weld defect.

To summarise, in light of what described above, the modelling block 12 is configured to execute a first classification, adapted to identify the presence or the absence of a weld defect (thus, using the first group of normalised values $d_{set}'$), through the trained model $M_1$, and a second classification, adapted to identify the type of defect if the first classification identified a weld defect (thus, using the first group of defect values $d_{set,d}'$ and the second group of defect values $d_{set,d}'''$, the latter used for the validation of the trained model $M_2$), through the trained model $M_2$.

At the end of the steps 25-27 of FIG. 4 and of the steps 33-37 of FIG. 7, the modelling block 12 determines the trained models $M_1$, $M_2$.

Again with reference to FIG. 2, the training step is followed by the inference step (step 23), wherein the inference block 13 receives from the normalisation block 8 the second group of normalised values $d_{set}''$, as well as the trained models $M_1$, $M_2$ determined in the previous training step and applies the latter to the aforementioned second groups of normalised values $d_{set}''$. In this manner, the inference block 13 classifies the second group of normalised values $d_{set}''$ relative to the features G associated with the second group of metallic components 2 by means of the aforementioned trained models $M_1$, $M_2$.

In particular, the second group of normalised values $d_{set}''$ is firstly classified by means of the trained model $M_1$, so that each normalised value $d_{set}''$ is classified according to the classes $C_1$ or $C_2$; subsequently, the normalised values $d_{set}''$ classified according to the class $C_1$ (i.e. indicative of metallic components 2 having weld defects), which form a third group of defect values $d_{set,d}''$, are furthermore classified by means of the trained model $M_2$, so that the metallic components 2 having weld defects are classified based on the type of weld defect (classes $C_3$-$C_5$).

In other words, since the label of each metallic component 2 of the second group of metallic components 2 is not made known to the inference block 13, the aforementioned trained models $M_1$, $M_2$ are applied in succession to a dataset whose classification is known but unknown to the aforementioned trained models $M_1$, $M_2$, so as to classify and compare the classification produced by the trained models $M_1$, $M_2$ with the labels actually applied to the metallic components 2 identified by the second groups of normalised values $d_{set}''$. More specifically, the classification obtained respectively from the trained models $M_1$, $M_2$ produces respective values representative of the probabilities that a sample metallic component 2 belongs to one of the classes considered ($C_1$ and $C_2$ in the case of classification based on two classes and $C_3$-$C_5$ in the case of classification based on three classes).

Starting from the probabilities obtained, the classes with higher probability for each type of classification (i.e. based on two or three classes) are selected as classification output of the system 5.

Once obtained the classification from the trained models $M_1$, $M_2$, step 24, the inference block 13 generates the inference data $d_{inf}$, which are thus indicative of the classifications made by the trained models $M_1$, $M_2$; subsequently, such inference data $d_{inf}$ are transmitted to the computation block 14, which is configured to determine quantities indicative of the quality of the classification executed at the previous step; in particular, the computation block 14 is configured to determine the corresponding output data $d_{out}$, which comprise respective accuracy A, precision P and recall R, defined according to the equations (1), (2) and, respectively, (3). In particular, in this step, with the purpose to evaluate the classification executed by the training block 10, the labels associated with the metallic components 2 represented by the second group of normalised values $d_{set}''$ are used for the determination of the quantities tp, fp, tn, fn and, thus, the accuracy, the precision P and the recall R.

In such regard, the Applicant verified that, in the case of classification based on two classes $C_1$, $C_2$, the trained model $M_1$ has an accuracy A equal to 89.88%, a precision P equal to 87.61% and a recall R equal to 83.72%, assumed an error for each of the aforementioned quantities equal to ±0.01%. Furthermore, the Applicant verified that, in the case of classification based on three classes $C_3$-$C_5$, the trained model $M_2$ has an accuracy A equal to 95.39%, a precision P equal to 93.89% and a recall R equal to 93.40%, assumed an error for each of the aforementioned quantities equal to ±0.01%.

Subsequently, the computation block 14 transmits the output data $d_{out}$ to the display 6, so as to make them displayable to the specialised expert. Furthermore, the trained models $M_1$, $M_2$ are stored in the memory 15.

The second operating step is now described, wherein the trained models $M_1$, $M_2$ (got from the memory 15) are applied to the values $d_G$ relative to the features G associated with the metallic components 52 whose labelling is not known with reference to FIG. 6. In other words, in the second operating step, the system 5 monitors the values $d_G$ of the features G associated with the metallic components 52 during one or more welding operations of the welding machinery 1 and classifies them using the trained models $M_1$, $M_2$.

Initially, step 28, the sensor elements 3 detect the features G associated with each metallic component 52 in a corresponding time instant $t_k$ belonging to the time interval Δt; in particular, the features G associated with each metallic component 52 comprise, analogously to the features G associated with the metallic components 2, the voltage V at the ends of the welding arc, the welding current A, the flow of cooling water ($H_2O$) $\varphi_{H2O}$, the shielding gas flow $\varphi_g$ for the weld pool, the feeding speed $v_f$ of the filler wire, the frequency $f_w$ of the kinematic oscillation of the torch, the amplitude $A_w$ of the oscillation itself and, the feeding speed $v_w$ of the torch relative to the welding machinery 1 when the latter operates on the metallic components 52. Furthermore, the time interval Δt represents, analogously to what described with reference to the first step (step 18), the time used by the welding machinery 1 for performing the welding operations on the single metallic component 52.

Subsequently, the sensor elements 3 generate the corresponding values $d_G$ of the features G as well as the corresponding time instant $t_k$ belonging to the time interval Δt associated with the respective metallic component 52, and transmits them to the system 5, which receives them at the input block 7 (step 29).

Then, step 30, the input block 7 transmits the values $d_G$ received to the normalisation block 8, which temporally normalises analogously to what described with reference to the values $d_G$ of the features G associated with the metallic components 2 (step 20 of FIG. 2).

The normalisation step carried out by the normalisation block 8 generates the corresponding normalised values of the values $d_G$, indicated as $d_{set}'''$, which represent as well the features G associated with each metallic component 52.

More specifically and analogously to the normalised values $d_{set}$, the normalised values $d_{set}'''$ are representative of temporal series (i.e. a sequence of the temporal instants $t_k$ of the corresponding time interval Δt) which describe the features G associated with each metallic component 52. The labels relative to the latter are still unknown. Such normalised values $d_{set}'''$ are thus stored in the hardware support 9 and transmitted to the classification block 11, in particular to the inference block 16.

Subsequently, step 31, the inference block 16 is configured to receive the normalised values $d_{set}'''$ from the normalisation block 8 and the trained models $M_1$, $M_2$ from the memory 15 and to apply the latter to the normalised values $d_{set}'''$, analogously to what described with reference to the step 23 of the method of FIG. 2; in other words, the inference block 16 applies the trained models $M_1$, $M_2$ to an unknown dataset (i.e. the normalised values $d_{set}'''$) and it is wanted to have an accurate prediction thereof, in particular relatively to the presence of a weld defect (in the case of a classification based on two classes $C_1$, $C_2$) and, in the case of presence of a weld defect, to the type of weld defects (in the case of a classification based on three classes $C_3$-$C_5$) according to the modes described with reference to the training block 10 on the occasion of the first operating step. In other words, also for the normalised values $d_{set}'''$, the classification block 11 applies the trained model $M_1$ in order to discriminate between features G relative to metallic components 52 having weld defects (i.e. the normalised values $d_{set}'''$ relative to metallic components 52 having weld defects) and not having weld defects; furthermore, the classification block 11, following the classification performed by the trained model $M_1$, applies the trained model $M_2$ on the normalised values $d_{set}'''$ relative to metallic components 52 having weld defects, so as to execute a further discrimination, which is relative to the type of weld defect identified on each metallic component 52 considered.

After applying the trained models $M_1$, $M_2$, step 32, the inference block 16 generates corresponding inference data $d_{inf}'$ based on the normalised values $d_{set}'''$; in particular, the inference data $d_{inf}'$ associated with the metallic components 52 are transmitted to the transmission block 17, which generates the corresponding output data $d_{out}'$ based on the aforementioned inference data $d_{inf}'$. In particular, the output data $d_{out}'$ associated with the metallic components 52 are transmitted from the transmission block 17 to the display 6, so as to make them displayable to the specialised expert. In this manner, the system 5 signals to the specialised expert if the welding machinery 1 is correctly performing the welding operations. In other words, the system 5 carries out a real-time check of the aforementioned welding operations, i.e. is configured to process the values $d_G$ assumed by the plurality of features G, acquired during the execution of the welding on each metallic component 52 according to the modes above described in a lapse of time (inferior to the time interval Δt) so as to establish the probabilities of belonging of the outcome of the current welding on the metallic component 52 to each of the classes $C_1$-$C_5$ of the plurality of classes C, so that the system 5 does not thus wait for the end of the current welding of each metallic component 52 but that, during the same welding, checks that the machinery 1 is correctly performing the current welding. Consequently, the system 5 is configured to predict the quality of the current welding based on the probabilities of belonging to each of the classes $C_1$-$C_5$ of the plurality of classes C, since, starting from such probability, the system 5 is capable of providing a feedback to the user on the outcome of the current welding in the aforementioned lapse of time; in the light of such feedback, the system 5, autonomously or on command of the user, can modify the values $d_G$ assumed by the plurality of features G and, thus modify the actual final outcome of the current welding on the metallic component 52. In short, the system 5 is configured to monitor the features of functioning of the machinery 1 and, thus, the progress of the welding operation on the metallic component 52. The system 5 is of predictive nature, i.e. allows, based on the values $d_G$, verifying in short time whether the machinery 1 is correctly performing (i.e. without generating weld defects, whatever their nature) the welding on the metallic components 52; such check is executed constantly, i.e. in real time, so that each metallic component 52 is welded correctly, thus sensibly reducing the incidence of weld defects.

When, in an alternative embodiment, the operations described with reference to the steps 28-30 are repeated up to the end of the welding operations of the metallic components 52 and, thus, the corresponding normalised values $d_{set}'''$ are stored in the hardware support 9 at the end of the welding operations and analysed only at the end of these; in other words, in such case, the analysis is carried out downstream of the welding operations. Such embodiment is advantageously usable when, for example, the system 5 is not capable of operating in real time (temporarily or not) or in the case where the welding machinery 1 is not equipped with a connection that enables the sharing in real time but that on the other hand allows the storing of the values of the features G detected. In this case, the classification made by the system 1 allows determining the welding goodness downstream; therefore, such embodiment allows both validating the trained models $M_1$, $M_2$ identified and updating them, i.e. train it on new values detected (i.e. on new first groups of normalised values $d_{set}'$ and of defect values $d_{set,d}'$, which can have labels provided by an expert).

The aforementioned method and the relative system have several advantages.

In particular, as previously anticipated, the system 5 allows determining the decision rules that adjust the relationship between the sample metallic components 2 and the labels associated therewith; in this manner, identifying such relation, represented by the trained models $M_1$, $M_2$, and verifying it on a group of sample data (i.e. the second group of normalised values $d_{set}''$ for the trained model $M_1$ and the third group of defect values $d_{set,d}''$ for the trained model $M_2$), the system 5 is capable of executing and evaluating the quality of the classification made by the trained models so that, once optimised, the latter can be used on unknown metallic components 52 for example for monitoring the welding when the welding machinery 1 operates on the latter. In other words, the application of trained models $M_1$, $M_2$ on an unknown dataset allows, when the application takes place on data acquired in real time, executing predictions on the quality of the welding performed by the welding machinery 1, i.e. monitoring the welding process of the welding machinery 1.

In addition, the present system 5 and the relative method are configured to monitor different features relative to the functioning of the welding machinery 1; in particular, such features are detected by respective sensor elements 3, which are mounted directly on the welding machinery 1 and thus are not external to the machinery 1. Such detection allows obtaining better performances with respect to the known systems, which mainly rely on external systems for the monitoring of the functioning of the welding machinery 1, since they are less subjected to phenomena of noise or distortion which could compromise the evaluation by the trained models $M_1$, $M_2$. Therefore, this characteristic makes the aforementioned method and the aforementioned system particularly advantageous to be applied in the industrial field.

Furthermore, the trained models $M_1$, $M_2$, obtained starting from the aforementioned values $d_G$ of the features G associated with the metallic components 2, are optimised by means of various optimisation techniques and are robust, since they are obtained by means of a machine learning algorithm based on the random forest approach, which provides a classification with improved characteristics, in particular in terms of accuracy, precision and recall.

Finally, it is evident that modifications and variants can be made to the method and to the system for monitoring and predicting described and illustrated herein without thereby departing from the scope of protection of the present invention, as claimed in the appended claims.

For example, the number of features G and, consequently, the number of sensor elements 3 can be greater than eight.

Furthermore, the number of trees of the first and of the second random forests $F_1$, $F_2$ can be greater than four.

Furthermore, the metallic components 2, 52 or the type of welding performed by the welding machinery 2 can be different; for example, such metallic components 2, 52 can be crossbeams, frames, subassemblies or engines.

In addition, the type of welding machinery 2 can be different; for example, depending on the type of metallic components 2, 52 (for example, crossbeams, frames, subassemblies or engines) to be welded, arms, torches, interfaces and welding processes used by the welding machinery 1 can vary.

Furthermore, the number of classes of the plurality of classes C can be different; for example, in the case where the metallic components 2, 52 are engines, the plurality of classes C can comprise a class relative to the type of defect called porosity defect.

In addition, in the case where the random forest approach is used for a regression instead of for a classification, i.e. the system 5 executes a prediction on an infinite number of classes (for example, a real numeric value comprised in an interval, for example between zero and one) instead of a finite number of classes (for example, $C_1$ and $C_2$), the modelling block 12 will consider defect measures, for example a degree of defectness for a specific class, instead of single labels pre-applied by an expert; in this case, the procedure described with reference to FIGS. 2, 4, 6 and 7 is substantially the same and the system 5 will determine as many trained models as the classes used for the regression procedure and thus for the determination of the degree of defectness for each type of class.

Finally, the modelling block 12 is capable of operating also using an algorithm of the not supervised type, i.e. wherein the labels associated with the metallic components 2 are not known a priori. In such case, the system 5 determines a single model that, in training step, allows defining groups or clusters of features G at the time instants $t_k$ which are similar to each other. Specifically, the goodness of the clusterisation is measured according to one or more metrics which evaluate the degree of intra-cluster homogeneity and their degree of extra-cluster separation. Such approach is characterised by the type of clustering algorithm (for example, a clustering algorithm such as K-means), a selection of a measure of distance between features G in different time instants $t_k$ and a metric of evaluation, the latter representing a measurement of the error of association between cluster and features G at the time instant $t_k$.

The modelling block 12 implementing the aforementioned methodology thus generates a label of belonging to a cluster or a probability of belonging to each cluster; furthermore, the label associated with each cluster is identified by a specialised user.

LIST OF THE REFERENCE NUMERALS OF THE FIGURES 1 welding machinery
2 metallic components
3 sensor elements
4A-4H sensors
5 system for monitoring and predicting
6 display
7 input block
8 normalisation block
9 hardware support
10 training block
11 classification block
12 modelling block
13 inference block
14 computation block
15 memory
16 inference block
17 transmission block
18 step
19 step
20 step
21 step
22 step
23 step
24 step
25 step
26 step
27 step
28 step
29 step
30 step
31 step
32 step
33 step
34 step
35 step
36 step
37 step
38 step
39 step
52 metallic components
$M_1$, $M_2$ trained models
G features
$d_G$ values
V voltage at the ends of the welding arc
A welding current
$\varphi_{H2O}$ flow of cooling water
$\varphi_g$ shielding gas flow for the weld pool
$v_f$ feeding speed of the filler wire
$f_w$ frequency of the kinematic oscillation of the torch
$A_w$ amplitude of the kinematic oscillation of the torch
$v_w$ feeding speed of the torch
$d_{set}$ normalised values
$d_{set}'$ first group of normalised values
$d_{set}''$ second group of normalised values
$d_{set,d}'$ first group of defect values
$d_{set,d}'''$ second group of defect values
$d_{set,d}''$ third group of defect values
$d_{inf}$, $d_{inf}'$ inference data
$d_{out}$, $d_{out}'$ output data
C plurality of classes
$\Delta t$ time interval
$t_k$ time instant
C plurality of classes
$C_1$-$C_5$ classes
$N_T$, $N_T'$ number of decision trees
$F_1$, $F_2$ random forests
$T_1$-$T_8$ decision trees
$A_1$-$A_8$ sets
J hyper-parameters
H maximum height of each decision tree
$n_{1-8,a-g}$ nodes
A accuracy
P precision
R recall
tp true positive
tn true negative
fp false positive
fn false negative
$t_m$ time instant
$d_{set}'''$ normalised values

The invention claimed is:

1. A method for monitoring and identifying, in real time, a quality of a welding performed by a welding machinery on a metallic component, the method comprising:
   initiating a current welding operation on a metallic component at the welding machinery;
   establishing, at a processing system, a plurality of classes (C; $C_1$-$C_5$) that describe possible weld defects on metallic components;
   identifying, at the processing system, a plurality of features (G) that characterise the current welding operation on the metallic component conducted using the welding machinery;
   acquiring, via an input block at the processing system from one or more sensors, a plurality of values ($d_G$) assumed by the plurality of identified features (G) during the current welding operation on the metallic component;
   processing, at the processing system, the acquired values (dG) assumed by the plurality of identified features (G) during the current welding operation on said metallic component to establish respective probabilities of an outcome of the current welding operation of belonging to each of the plurality of established classes (C; $C_1$-$C_5$) that describe possible weld defects on the metallic component and to predict a possible presence of a weld defect on the metallic component based on said respective probabilities;
   outputting, at a display of the processing system, output data indicative of a quality of the respective probabilities of belonging to the each of the plurality of established classes; and modifying one or more of the values ($d_G$) to modify a final outcome of the current welding operation on said metallic component based on the quality of the respective probabilities of belonging to the each of the plurality of established classes, wherein said features (G) are physical quantities relative to the functioning of the welding machinery during the current welding operation, and wherein the method further comprises temporally normalising, at a normalisation block of the processing system, the plurality of values ($d_G$) assumed by the plurality of identified features (G) so as to determine respective normalised values ($d_{set}$, $d_{set}'$, $d_{set}''$, $d_{set,d}$, $d_{set,d}'$, $d_{set,d}''$, $d_{set,d}'''$; $d_{set}'''$) that are provided to the processing system for monitoring and identifying the quality.

2. The method according to claim 1, wherein the plurality of values ($d_G$) assumed by the plurality of identified features (G) are detected by sensor elements mounted on the welding machinery.

3. The method according to claim 1, wherein the identified features (G) comprise: a voltage (V) at ends of a welding arc, a welding current (A), a flow of cooling water ($\varphi_{H2O}$), a shielding gas flow ($\varphi_g$) for a weld pool, a feeding speed ($v_f$) of a filler wire, a frequency ($f_w$) of a kinematic oscillation of a torch, an oscillation amplitude ($A_w$) and a feeding speed ($v_w$) of the torch.

4. A method for monitoring and identifying, in real time, a quality of a welding performed by a welding machinery on a metallic component, the method comprising:

initiating a current welding operation on a metallic component at the welding machinery;

establishing, at a processing system, a plurality of classes (C; $C_1$-$C_5$) that describe possible weld defects on metallic components;

identifying, at the processing system, a plurality of features (G) that characterise the current welding operation on the metallic component conducted using the welding machinery;

acquiring, via an input block at the processing system from one or more sensors, a plurality of values ($d_G$) assumed by the plurality of identified features (G) during the current welding operation on the metallic component;

processing, at the processing system, the acquired values ($d_G$) assumed by the plurality of identified features (G) during the current welding operation on said metallic component to establish respective probabilities of an outcome of the current welding operation of belonging to each of the plurality of established classes (C; $C_1$-$C_5$), that describe possible weld defects on the metallic component and to predict a possible presence of a weld defect on the metallic component based on said respective probabilities;

outputting, at a display of the processing system, output data indicative of a quality of the respective probabilities of belonging to the each of the plurality of established classes; and modifying one or more of the values ($d_G$) to modify a final outcome of the current welding operation on said metallic component based on the quality of the respective probabilities of belonging to the each of the plurality of established classes, wherein said features (G) are physical quantities relative to the functioning of the welding machinery during the current welding operation, wherein the processing of the plurality of values (dG) assumed by the plurality of identified features (G) comprises:

acquiring, at a training block of the processing system (5), another plurality of values ($d_{set}$, $d_{set}'$, $d_{set}''$, $d_{set,d}$, $d_{set,d}'$, $d_{set,d}'''$) assumed by the plurality of identified features (G) during welding operations on a group of first metallic components and on a group of second metallic components;

providing, at a training block of the processing system, the acquired values ($d_G$, $d_{set}$, $d_{set}'$, $d_{set}''$, $d_{set,d}$, $d_{set,d}'$, $d_{set,d}'''$) assumed by the plurality of identified features (G) during welding operations on each first metallic component to the processing system so as to determine at least one trained model ($M_1$, $M_2$); and processing, at an inference block of the processing system, the acquired values ($d_G$, $d_{set}$, $d_{set}'$, $d_{set}''$, $d_{set,d}$, $d_{set,d}'$, $d_{set,d}''$) assumed by the plurality of identified features (G) during welding operations on said second metallic components) with said at least one trained model ($M_1$, $M_2$) to establish said respective probabilities.

5. The method according to claim 4, further comprising:

inspecting a final outcome of the welding operation on a second metallic component to manually assign at least one corresponding class (C; $C_1$-$C_5$); and verifying, for said second metallic component, whether the at least one class (C; $C_1$-$C_5$) having a highest probability established by the processing system coincides with the manually assigned at least one class (C; $C_1$-$C_5$) in order to establish a reliability of the processing system.

6. The method according to claim 4, wherein the plurality of classes comprise first and second classes relative to a presence of a weld defect and, respectively, to a type of defect if the weld defect is present, and wherein the providing of the acquired values ($d_G$, $d_{set}$, $d_{set}'$, $d_{set}''$, $d_{set,d}$, $d_{set,d}'$, $d_{set,d}'''$) assumed by the plurality of identified features (G) is carried out so as to determine a first and a second trained model ($M_1$, $M_2$) and comprises:

determining a first number (NT) of decision trees ($T_1$-$T_4$) not correlated with each other, each decision tree ($T_1$-$T_4$) being relative to a random combination ($A_1$-$A_4$) of values ($d_G$, $d_{set}$, $d_{set}'$, $d_{set}''$) assumed by the plurality of identified features (G) for each first metallic component, the decision trees forming a first random forest ($F_1$);

classifying each combination ($A_1$-$A_4$) of the values ($d_G$, $d_{set}$, $d_{set}'$, $d_{set}''$) for each decision tree ($T_1$-$T_4$) based on a first subset of classes ($C_1$, $C_2$) of the plurality of classes (C);

executing a majority classification of the first random forest ($F_1$) based on the classification made by each decision tree ($T_1$-$T_4$), the classification of the first random forest ($F_1$) being determined based on a number of the decision trees ($T_1$-$T_4$) of the first random forest ($F_1$) that classify the values ($d_G$, $d_{set}$, $d_{set}'$, $d_{set}''$) assumed by the plurality of identified features (G) for the group of first metallic components with a same class belonging to the first subset of classes ($C_1$, $C_2$) of the plurality of classes (C); and determining a first trained model ($M_1$) according to the classification associated with the first random forest ($F_1$), the first trained model ($M_1$) being configured to distinguish between second metallic components belonging to a first class ($C_1$) relative to a presence of weld defects and second metallic components belonging to a second class ($C_2$) relative to an absence of weld defects, the second metallic components belonging to the first class being represented by defect values ($d_{set,d}$).

7. The method according to claim 6, further comprising:
acquiring defect values ($d_{set,d}$);
dividing the defect values into a first group of defect values ($d_{set,d}'$) and a second group of defect values ($d_{set,d}'''$) distinct from one another;
determining a second number ($N_T'$) of decision trees ($T_5$-$T_8$) not correlated with each other, each decision tree ($T_5$-$T_8$) being relative to a random combination ($A_5$-$A_8$) of the first group of defect values assumed by the plurality of identified features (G) for each first metallic component, the second number of decision trees forming a second random forest ($F_2$);
classifying each combination ($A_5$-$A_8$) of the defect values ($d_{set,d}$, $d_{set,d}'$, $d_{set,d}''$) for each decision tree ($T_5$-$T_8$) based on a second subset of classes ($C_3$-$C_5$) of the plurality of classes (C), independent of the first subset of classes of the plurality of classes;
executing a majority classification of the second random forest ($F_2$) based on the classification made by each of the second number of decision trees ($T_5$-$T_8$), the classification of the second random forest ($F_2$) being determined based on a number of the second number of decision trees ($T_5$-$T_8$) of the second random forest that classify the defect values ($d_{set,d}$, $d_{set,d}'$) assumed by the plurality of identified features (G) for the group of first metallic components with a same class belonging to the second subset of classes ($C_3$-$C_5$) of the plurality of classes (C); and
determining a second trained model ($M_2$) according to the classification associated with the second random forest ($F_2$), the second trained model ($M_2$) being configured to classify the first metallic components according to a type of weld defect.

8. The method according to claim 7, wherein the determining of the first number ($N_T$) of decision trees ($T_1$-$T_4$) comprises:
defining at least one feature (J) configured to optimise the determining of the first trained model ($M_1$), the at least one feature (J) being indicative of a characteristic relative to each decision tree ($T_1$-$T_4$) of the first random forest ($F_1$); and
verifying that the at least one feature optimises at least one metric relative to the first trained model by means of a cross-validation,
and wherein the determining of the second number ($N_T'$) of decision trees ($T_5$-$T_8$) comprises:
defining the at least one feature (J) configured to optimise the determining of the second trained model ($M_2$); and
verifying that the at least one feature optimises at least one metric relative to the second trained model by means of a cross-validation.

9. The method according to claim 8, wherein the at least one feature (J) is one of the first and second numbers of decision trees in the first and second random forests, a maximum height (H) of the respective decision trees of the first and second random forests, the number of defect values ($d_{set}$, $d_{set}'$, $d_{set}''$, $d_{set,d}$, $d_{set,d}'$, $d_{set,d}'''$), a number of features (G) used for the construction of the combinations ($A_1$-$A_8$) of the defect values, a minimum number of values that must be located in a leaf of each decision tree ($T_1$-$T_8$), a minimum number of values required to split a node of the respective decision trees into children nodes and a criterion of impurity.

10. The method according to claim 7, wherein the determining of the first number ($N_T$) of decision trees ($T_1$-$T_4$) comprises:
defining second features (J) configured to optimise the determining of the first trained model ($M_1$), the second features (J) being indicative of a characteristic relative to each decision tree ($T_1$-$T_4$) of the first random forest ($F_1$); and
verifying that the second features optimise at least one metric relative to the first trained model by means of a cross-validation,
and wherein the determining the second number ($N_T'$) of decision trees ($T_5$-$T_8$) comprises:
defining the second features (J) configured to optimise the determining of the second trained model ($M_2$); and
verifying that the second features optimise at least one metric relative to the second trained model by means of a cross-validation.

11. The method according to claim 10, wherein the second features (J) comprise the first and second numbers of decision trees in the first and second random forests, a maximum height (H) of the respective decision trees of the first and second random forests, the number of defect values ($d_{set}$, $d_{set}'$, $d_{set}''$, $d_{set,d}$, $d_{set,d}'$, $d_{set,d}'''$), a number of features (G) used for the construction of the combinations ($A_1$-$A_8$) of the defect values, a minimum number of values that must be located in a leaf of each decision tree ($T_1$-$T_8$), a minimum number of values required to split a node of the respective decision trees into children nodes and a criterion of impurity.

12. The method according to claim 5, wherein the verifying, for each second metallic component, whether the at least one class (C; $C_1$-$C_5$) having the highest probability established by the processing system coincides with the manually assigned at least one class (C; $C_1$-$C_5$) comprises determining a plurality of quantities (A, P, R) which comprise accuracy (A), precision (P) and recall (R) calculated by evaluating a number of false positives, false negatives, true positives and true negatives classified by the trained models ($M_1$, $M_2$) when applied to the values ($d_G$, $d_{set}$, $d_{set}'$, $d_{set}''$, $d_{set,d}$, $d_{set,d}'$, $d_{set,d}'''$) of the plurality of features (G) of the second metallic components (2).

13. A system for monitoring and identifying the quality of a welding of a welding machinery on a metallic component, the welding machinery being couplable to the system for monitoring and identifying the quality; the system for monitoring and identifying the quality being configured to carry out the method according to claim 1.

* * * * *